(12) United States Patent
Jang

(10) Patent No.: US 8,308,773 B2
(45) Date of Patent: Nov. 13, 2012

(54) PEDICLE SCREW

(75) Inventor: Jong Wuk Jang, Seoul (KR)

(73) Assignee: Medyssey Co., Ltd. (KR)

( * ) Notice: Subject to any disclaimer, the term of this patent is extended or adjusted under 35 U.S.C. 154(b) by 1024 days.

(21) Appl. No.: 11/993,814

(22) PCT Filed: Dec. 14, 2006

(86) PCT No.: PCT/KR2006/005477
§ 371 (c)(1),
(2), (4) Date: Dec. 21, 2007

(87) PCT Pub. No.: WO2007/073059
PCT Pub. Date: Jun. 28, 2007

(65) Prior Publication Data
US 2010/0087874 A1    Apr. 8, 2010

(30) Foreign Application Priority Data

Dec. 21, 2005 (KR) .................. 20-2005-0035851

(51) Int. Cl.
*A61B 17/70* (2006.01)
(52) U.S. Cl. ......... 606/270; 606/265; 606/272; 606/308
(58) Field of Classification Search .............. 606/264, 606/265, 271, 272, 275, 301–308, 270, 246; 411/265, 272, 290, 288, 291, 421, 417, 916
See application file for complete search history.

(56) References Cited

U.S. PATENT DOCUMENTS

| | | | |
|---|---|---|---|
| 1,352,765 A * | 9/1920 | Sevigne | ................. 411/291 |
| 4,887,596 A | 12/1989 | Sherman | |
| 4,917,409 A | 4/1990 | Reeves | |
| 5,154,719 A | 10/1992 | Cotrel | |
| 5,176,680 A | 1/1993 | Vignaud et al. | |
| 5,217,497 A | 6/1993 | Mehdian | |
| 5,306,275 A | 4/1994 | Bryan | |
| 5,360,431 A | 11/1994 | Puno et al. | |
| 5,443,467 A | 8/1995 | Biedermann et al. | |
| 5,466,237 A | 11/1995 | Byrd, III et al. | |

(Continued)

FOREIGN PATENT DOCUMENTS

JP    2002-052030 A    2/2002

(Continued)

OTHER PUBLICATIONS

Written Opinion of the International Searching Authority dated Jun. 8, 2007 in Int'l Application No. PCT/KR2006/005477.

*Primary Examiner* — David Isabella
*Assistant Examiner* — Suba Ganesan
(74) *Attorney, Agent, or Firm* — Matthew B. Dernier, Esq.; Gibson & Dernier LLP

(57) ABSTRACT

Disclosed is a pedicle screw. By changing the structure of a threaded portion of a locking bolt engaged with a head of the pedicle screw and forming a groove on the locking bolt, the threaded portion is pressed in a fastening direction of the locking bolt, so that when a head of the pedicle screw is fastened to the locking bolt, a fixation cap is not released by the force applied from the head expanding towards an outside, and thus the locking bolt is easily fastened to the head of a screw body, thereby improving an inefficiency factor such as delay of surgical operation time due to release or interference of the fixation cap.

10 Claims, 4 Drawing Sheets

U.S. PATENT DOCUMENTS

| | | | |
|---|---|---|---|
| 5,474,555 A | 12/1995 | Puno et al. | |
| 5,486,174 A | 1/1996 | Fournet-Fayard et al. | |
| 5,520,689 A | 5/1996 | Schlapfer et al. | |
| 5,536,268 A | 7/1996 | Griss | |
| 5,669,911 A | 9/1997 | Errico et al. | |
| 5,683,390 A | 11/1997 | Metz-Stavenhagen et al. | |
| 5,702,443 A * | 12/1997 | Brånemark | 606/314 |
| 5,738,685 A | 4/1998 | Halm et al. | |
| 5,752,957 A | 5/1998 | Ralph et al. | |
| 5,782,833 A | 7/1998 | Haider | |
| 5,876,403 A | 3/1999 | Shitoto | |
| 5,989,254 A | 11/1999 | Katz | |
| 6,074,391 A | 6/2000 | Metz-Stavenhagen et al. | |
| 6,113,601 A | 9/2000 | Tatar | |
| 6,139,549 A | 10/2000 | Keller | |
| 6,254,146 B1 | 7/2001 | Church | |
| 6,302,888 B1 | 10/2001 | Mellinger et al. | |
| 6,402,752 B2 | 6/2002 | Schaffler-Wachter et al. | |
| 6,537,276 B2 | 3/2003 | Metz-Stavenhagen | |
| 6,565,567 B1 | 5/2003 | Haider | |
| 6,626,908 B2 | 9/2003 | Cooper et al. | |
| 6,641,586 B2 | 11/2003 | Varieur | |
| 6,692,500 B2 | 2/2004 | Reed | |
| 6,723,100 B2 | 4/2004 | Biedermann et al. | |
| 6,736,820 B2 | 5/2004 | Biedermann et al. | |
| 6,835,196 B2 | 12/2004 | Biedermann et al. | |
| 6,869,433 B2 | 3/2005 | Glascott | |
| 6,974,460 B2 | 12/2005 | Carbone et al. | |
| 7,018,378 B2 | 3/2006 | Biedermann et al. | |
| 7,128,743 B2 | 10/2006 | Metz-Stavenhagen | |
| 7,214,227 B2 | 5/2007 | Colleran et al. | |
| 7,223,268 B2 | 5/2007 | Biedermann | |
| 7,250,052 B2 | 7/2007 | Landry et al. | |
| 7,291,153 B2 | 11/2007 | Glascott | |
| 7,377,923 B2 | 5/2008 | Purcell et al. | |
| 7,491,218 B2 | 2/2009 | Landry et al. | |
| 7,563,264 B2 | 7/2009 | Landry et al. | |
| 7,588,575 B2 | 9/2009 | Colleran et al. | |
| 7,618,442 B2 | 11/2009 | Spitler et al. | |
| 7,662,172 B2 | 2/2010 | Warnick | |
| 7,678,137 B2 | 3/2010 | Butler et al. | |
| 7,691,132 B2 | 4/2010 | Landry et al. | |
| 7,828,829 B2 | 11/2010 | Ensign | |
| 7,837,716 B2 | 11/2010 | Jackson | |
| 2002/0138076 A1 * | 9/2002 | Biedermann et al. | 606/61 |
| 2003/0100904 A1 * | 5/2003 | Biedermann | 606/73 |
| 2004/0082956 A1 * | 4/2004 | Baldwin et al. | 606/73 |
| 2004/0158247 A1 | 8/2004 | Sitiso et al. | |
| 2004/0172022 A1 | 9/2004 | Landry et al. | |
| 2005/0049589 A1 | 3/2005 | Jackson | |
| 2005/0131406 A1 | 6/2005 | Reiley et al. | |
| 2006/0009773 A1 | 1/2006 | Jackson | |
| 2006/0025767 A1 | 2/2006 | Khalili | |
| 2006/0058794 A1 | 3/2006 | Jackson | |
| 2006/0084996 A1 | 4/2006 | Metz-Stavenhagen | |
| 2006/0106383 A1 | 5/2006 | Biedermann et al. | |
| 2006/0142761 A1 | 6/2006 | Landry et al. | |
| 2006/0229615 A1 | 10/2006 | Abdou | |
| 2006/0247631 A1 | 11/2006 | Ahn et al. | |
| 2007/0055238 A1 | 3/2007 | Biedermann et al. | |
| 2007/0093818 A1 | 4/2007 | Biedermann et al. | |
| 2007/0260246 A1 | 11/2007 | Biedermann | |
| 2008/0177322 A1 | 7/2008 | Davis et al. | |
| 2008/0234752 A1 | 9/2008 | Dahners | |
| 2008/0288002 A1 | 11/2008 | Crall et al. | |
| 2009/0005814 A1 | 1/2009 | Miller et al. | |
| 2009/0005815 A1 | 1/2009 | Ely | |
| 2009/0093843 A1 | 4/2009 | Lemoine et al. | |
| 2009/0163956 A1 | 6/2009 | Biedermann et al. | |
| 2009/0163961 A1 | 6/2009 | Kirschman | |
| 2009/0228050 A1 | 9/2009 | Jackson | |
| 2009/0306722 A1 | 12/2009 | Lewis et al. | |
| 2010/0004694 A1 | 1/2010 | Little | |
| 2010/0094353 A1 | 4/2010 | Shim et al. | |
| 2010/0131018 A1 | 5/2010 | Konieczynski et al. | |
| 2010/0198264 A1 | 8/2010 | Metz-Stavenhagen | |
| 2010/0198273 A1 | 8/2010 | Kwak et al. | |
| 2010/0234904 A1 | 9/2010 | Richelsoph | |

FOREIGN PATENT DOCUMENTS

KR 20030015826 A 2/2003

* cited by examiner

PEDICLE SCREW

TECHNICAL FIELD

The present invention relates to a pedicle screw, and more particularly, to a pedicle screw, in which by changing the structure of a threaded portion of a locking bolt engaged with a head of the pedicle screw and forming a groove on the locking bolt, the threaded portion is pressed in a fastening direction of the locking bolt, so that when a head of the pedicle screw is fastened to the locking bolt, a fixation cap is not released by the force applied from the head expanding towards an outside, and thus the locking bolt is easily fastened to the head of a screw body, thereby improving an inefficiency factor such as delay of surgical operation time due to release or interference of the fixation cap.

BACKGROUND ART

Generally, a patient suffered from injured portion of spinal bones does not carry himself or herself in such a state. Even though a patient having a weak damage acts, the damaged spinal bone compresses adjacent spinal bone or comes into contact with adjacent spinal bone, thereby causing a pain in the patient. In addition, although the patient is placed under medical care, the recovery is delayed.

Therefore, the patient suffered from the ruptured or damaged spinal bone has a surgical operation on the adjacent spinal bones by supporting the damage spinal bone with an artificial prosthetic device so as to prevent the damaged spinal bone from being pressed or expanded.

Such an artificial prosthetic device consists of pedicle screws inserted into upper and lower portions of the damaged spinal bone to serve as a fixation, and a rod engaged to the pedicle screw to serve as a support.

FIG. 7 illustrates the structure of a conventional artificial prosthetic device.

Referring to FIG. 7, a pedicle screw 30 has an opening 32 formed on an upper portion of a head engaging groove 31, and a threaded portion 34 formed on inner surfaces or outer surfaces of support walls 33 provided on both sides of the opening. The support pipe 36 of an engaging member 35 is placed on the outer surface of the support wall 33, and then, a male threaded part 37 is threadedly engaged with the threaded portion. With the above arrangement, there is a problem in that a rod 20 is not horizontally placed. In addition, in case the rod 20 is inserted at an inclined angle, the rod 20 should be pressed against the head engaging groove 31 by using a separate guide tool, so that the engaging member 35 can be engaged to the pedicle screw by means of a screw and a ring or a cap.

More specifically, the rod 20 should be forcibly held in the engaging groove 31 by using the separate guide tool before the male threaded part 37 of the engaging member 35 is threadedly engaged with the threaded portion of the engaging groove 31. In addition, the rod can be pre-engaged by the male threaded part 37. As such, the weak fastening force of the threaded portion of the support wall can be complemented by the screw, the outer ring or the cap used on the outer portion of the engaging member. Since the use of the outer ring or cap increases a width of the engaging member, it may cause the interference between the components in a narrow space on the operation.

DISCLOSURE

Technical Problem

Accordingly, the present invention is directed to a pedicle screw that substantially obviates one or more problems due to limitations and disadvantages of the related art.

An object of the present invention is to provide a pedicle screw, in which by adjusting a thread angle of threaded portions formed on a locking bolt and a head of the pedicle screw and forming a groove on the locking bolt, the locking bolt is not released from the head, in which a fixation cap is not required to prevent the interference of a rod, in which a volume of the head is reduced, and in which the locking bolt is easily fastened to the pedicle screw, thereby improving precision and inefficiency factors such as delay of surgical operation time due to release or interference of the fixation cap.

Technical Solution

To achieve the object and other advantages, according to one aspect of the present invention, there is provided a pedicle screw including a screw body threadedly engaged with spinal bones at regular interval to support a rod against the spinal bone so as to prevent a damaged portion of the spinal bone from being expanded or pressed, the screw body having a head on an upper end of the screw body, a seat groove formed on a center portion of the head, an upper portion and both sides of the seat groove being opened, and a female threaded portion formed on an inner surface of the seat groove, and a locking bolt having a male threaded portion formed on an outer periphery thereof which is threadedly engaged with the female threaded portion to support the rod installed on the head of the screw body, wherein a groove is formed to have a predetermined depth on the outer periphery of the locking bolt in a spiral direction, so that the male threaded portion of the locking bolt closely contacts the female threaded portion of the head when the locking bolt is threadedly engaged with the head, so as to prevent the locking bolt from being released from the head.

The groove is formed to have a depth equal to a half of a diameter of the locking bolt.

In addition, the female threaded portion formed on the head and the male threaded portion formed on the locking bolt have a corresponding inversed-trapezoidal cross section.

Advantageous Effects

As described above, according to the pedicle screw of the present invention, the shape and design of the female threaded portion formed on the head of the screw body and male threaded portion of the locking bolt, and the groove formed on the locking bolt can prevent the release of the head, and easily rigidly fix the pedicle screw, without using a cap.

BRIEF DESCRIPTION OF THE DRAWINGS

The foregoing and other objects, features and advantages of the present invention will become more apparent from the following detailed description when taken in conjunction with the accompanying drawings in which.

BEST MODE

A preferred embodiment according to the present invention will now be explained with reference to the accompanying drawings.

Figure 1:
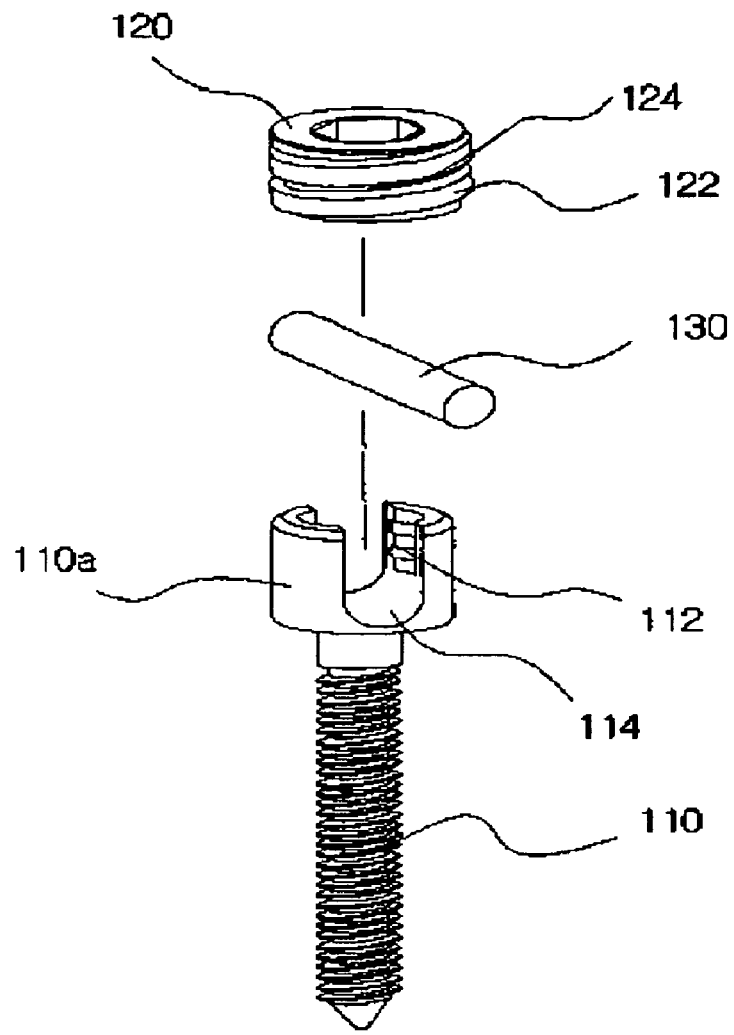
FIG. 1 is a perspective view illustrating the construction of a pedicle screw according to the present invention.
Figure 2:
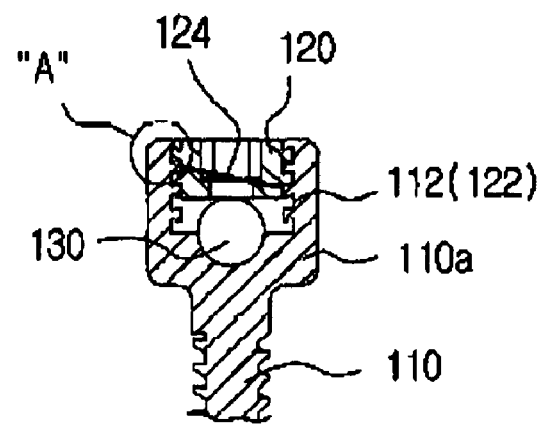
FIG. 2 is a front cross-sectional view illustrating the engaged state of a pedicle screw according to the present invention.
Figure 3:
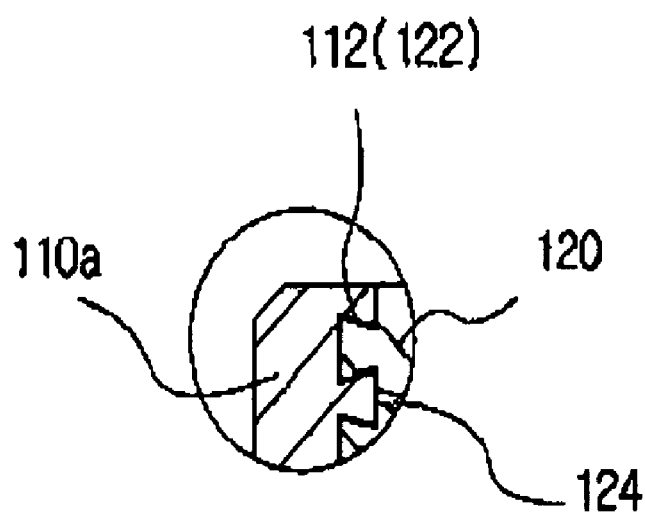
FIG. 3 is an enlarged cross-sectional view of the portion "A" in FIG. 2.
Figure 4:
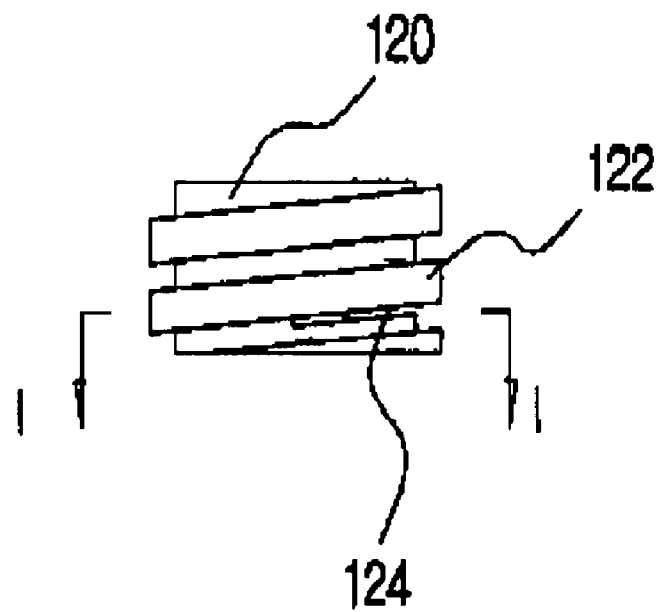
FIG. 4 is a view illustrating only a locking bolt of a pedicle screw according to the present invention.
Figure 5:
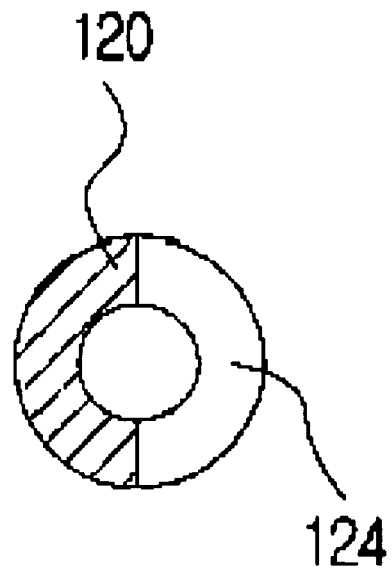
FIG. 5 is a cross-sectional view taken along a line I-I in FIG. 4.
Figure 6:
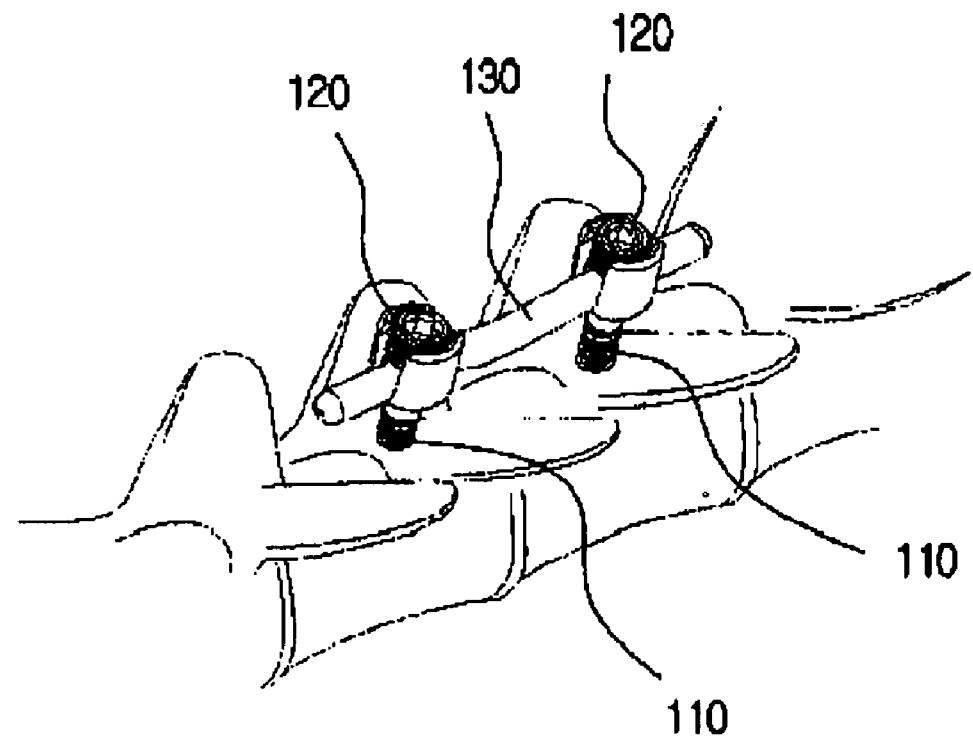
FIG. 6 is a perspective view illustrating the installed state of a pedicle screw according to the present invention.
Figure 7:
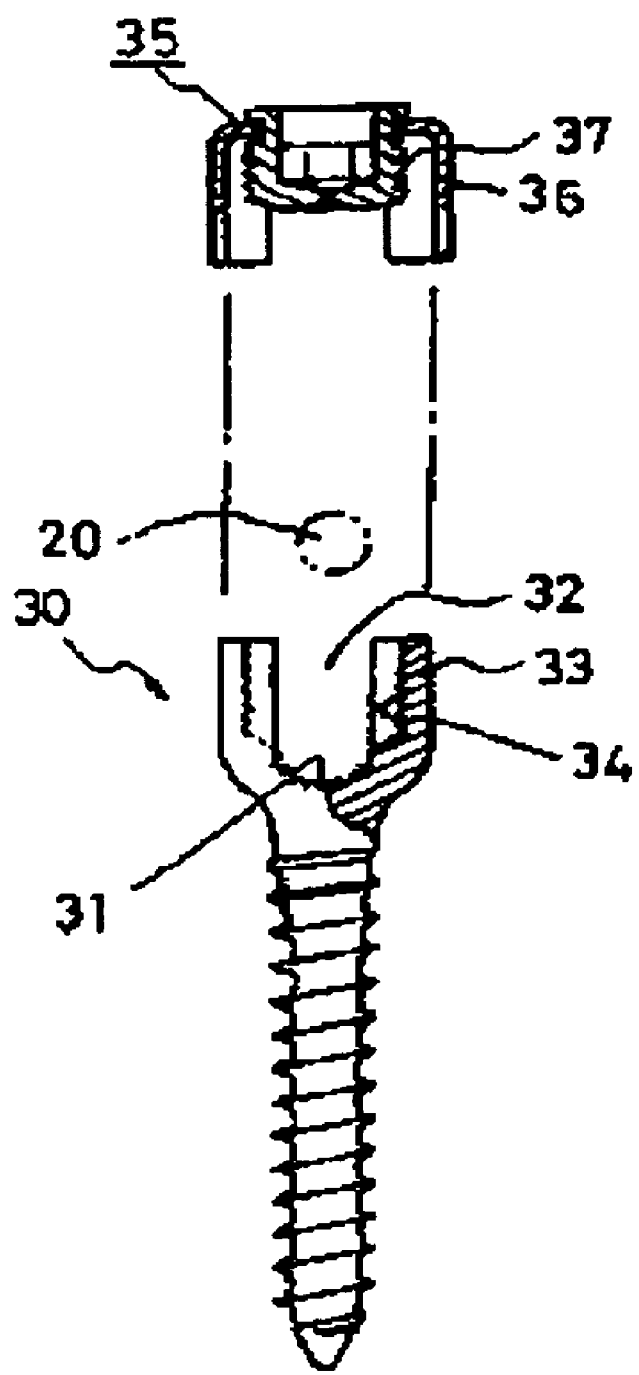
FIG. 7 is an exploded perspective view illustrating a conventional pedicle screw according to the present invention.

FIG. 1 is a perspective view illustrating the construction of a pedicle screw according to the present invention. FIG. 2 is a front cross-sectional view illustrating the engaged state of the pedicle screw according to the present invention. FIG. 3 is an enlarged cross-sectional view of the portion "A" in FIG. 2. FIG. 4 is a view illustrating only a locking bolt of a pedicle screw according to the present invention. FIG. 5 is a cross-sectional view taken along a line I-I in FIG. 4. FIG. 6 is a perspective view illustrating the installed state of a pedicle screw according to the present invention.

As shown in the figures, the pedicle screw according to the present invention includes a screw body 110. The screw bodies 110 are threadedly engaged with spinal bones at regular intervals. The screw body 110 has a head 110*a* on an upper end of the screw body, a seat groove 114 formed on a center portion of the head 110*a*, an upper portion and both sides of the seat groove being opened, and a female threaded portion 112 formed on an inner surface of the seat groove 114.

A rod 130 is installed on the seat groove 114 formed on the head 110*a* of the screw body 110, and has a locking bolt 120 for locking and supporting the rod 130. A male threaded portion 122 is formed on an outer periphery of the locking bolt 120, and is threadedly engaged with the female threaded portion 112 formed on the head 110*a* of the screw body 110.

As shown in FIG. 3, it is preferable that the female threaded portion 112 and the male threaded portion 122 have a corresponding inversed-trapezoidal shape so that the threaded portions are interconnected. The reason is to prevent the locking bolt 120 from being released from the head 100*a*.

As shown in the figures, the present invention is characterized in that the groove 124 is formed on the locking bolt 120. The locking bolt is not released from the head 110*a* by the groove 124. More specifically, the male threaded portion 122 formed on the locking bolt 120 is pressed towards one side of the female threaded portion 112 formed on the head 110*a*, and then, the threaded portions are engaged to each other to prevent the locking bolt 120 from being released from the head 110*a*.

The groove 124 is formed to have a predetermined depth on the outer periphery of the locking bolt 120 in a spiral direction. Consequently, the male threaded portion 122 formed on the locking bolt 120 is pressed towards one side of the female threaded portion 112 formed on the head 110*a*, and then, the threaded portions are engaged to each other to prevent the locking bolt 120 from being released from the head 110*a*. The groove 124 may be formed to have a depth equal to a half of a diameter of the locking bolt 120, but the present invention is not limited thereto. For example, the groove may be formed to have a depth equal to ⅓ of the diameter of the locking bolt 120. The above examples demonstrate that the depth of the groove 124 extends into a root of the locking bolt 120. The groove may be formed to have a depth in such a way that the male threaded portion 122 formed on the locking bolt 120 is pressed toward one direction by the groove 120. More particularly, the groove 124 is generally planar and extends radially inwardly from the male threaded portion 122 (male threads) and has a height less than the pitch of the male threaded portion 122. Further, the groove 124 can also be configured to extend through a body of the locking bolt 120 in a chord-like fashion and angled relative to a longitudinal axis of the body.

With the pedicle screw according to the present invention, the screw bodies 110 are threadedly engaged with the spinal bones at a regular interval. The rod 130 is inserted into the groove 114 formed on the head 110*a* of the screw body 110. Then, the rod is fixed by the locking bolt 120, thereby interconnecting the screw bodies 110 installed on the spinal bones at a regular interval.

In this instance, the female threaded portion 112 and the male threaded portion 122 formed on the head 110*a* of the screw body 110 which are engaged to each other have an inversed-trapezoidal shape, so as to prevent the male threaded portion 122 of the locking bolt 120 from being released from the female threaded portion 112 of the head 110*a*. As a result, the head 110*a* of the screw body 110 does not rotate, and the head 110*a* and the rod 130 are rigidly fixed by the locking bolt 120.

In particular, the pedicle screw of the present invention can be more rigidly fixed by the groove 124 formed on the locking bolt 120. When the locking bolt 120 is engaged with the head 110*a*, the force resulted from a bottom the locking bolt abutting the rod 130 is transferred to the male threaded portion 122 in a direction perpendicular to the fastening direction of the locking bolt 120 through the groove 124. Consequently, one surface of the male threaded portion 122 is closely engaged with the female threaded portion 112, thereby preventing the locking bolt 120 from being released from the head.

According to the present invention, the female threaded portion 112 and the male threaded portion 122 formed on the head 110*a* of the screw body 110 which are engaged to each other have an inversed-trapezoidal shape, and the groove 124 is formed on the locking bolt 120, so that the threaded portion are rigidly engaged with each other so as to prevent locking bolt 120 from being released from the head 110*a*.

FIG. 6 is a perspective view illustrating the installed state of the pedicle screw according to the present invention.

Referring to FIG. 6, the screw body 110 is threadedly engaged with the spinal bone, and the rod 114 is inserted into the seat groove 114 formed on the head 110*a* of the screw body 110. Then, the locking bolt 120 is fastened to the head 110*a*. At that time, the locking bolt 120 is turned to easily fix the rod 130. The design of the female threaded portion 112 formed on the head 110*a* of the screw body 110 and male threaded portion 122 of the locking bolt 120 and the groove formed on the locking bolt 120 can prevent the release of the locking bolt from the groove 124, so that a cap is not needed.

INDUSTRIAL APPLICABILITY

As can be seen from the foregoing, according to the pedicle screw of the present invention, the shape and design of the female threaded portion formed on the head of the screw body and male threaded portion of the locking bolt, and the groove formed on the locking bolt can prevent the release of the head, and easily rigidly fix the pedicle screw, without using a cap.

While this invention has been described in connection with what is presently considered to be the most practical and preferred embodiment, it is to be understood that the invention is not limited to the disclosed embodiment and the drawings. On the contrary, it is intended to cover various modifications and variations within the spirit and scope of the appended claims.

The invention claimed is:

1. A pedicle screw including:
   a screw body having:
   threads for engaging a spinal bone,
   a head on an upper end of the screw body, the head for supporting a rod relative to the spinal bone,
   a seat groove formed in the head, and an upper portion and both sides of the seat groove being open for receiving the rod, and
   a female threaded portion formed on an inner surface of the seat groove; and
   a locking bolt having:
   a male threaded portion formed on an outer periphery thereof which is threadedly engageable with the female threaded portion of the seat groove to engage and lock the rod to the head of the screw body, and
   a locking bolt groove formed within the locking bolt to have a predetermined depth on the outer periphery of the locking bolt in a spiral direction and extending radially inwardly from the male threaded portion into a root of the locking bolt.

2. The pedicle screw as claimed in claim 1, wherein the locking bolt groove is formed to have a depth equal to about a half of a diameter of the locking bolt.

3. The pedicle screw as claimed in claim 1, wherein the predetermined depth is between ⅓ and ½ of a diameter of the locking bolt.

4. The pedicle screw as claimed in claim 1, wherein the female threaded portion has a generally inversed-trapezoidal cross section.

5. The pedicle screw as claimed in claim 1, wherein when the locking bolt is engaged with the head and the rod, a force resulting from the rod abutting the locking bolt is transferred to the male threaded portion to more closely engage the male threaded portion with the female threaded portion.

6. A pedicle screw comprising:
   a screw body having:
   threads for engaging a spinal bone,
   a head on an upper end of the screw body, the head for supporting a rod relative to the spinal bone,
   a seat groove formed in the head, and an upper portion and both sides of the seat groove being open for receiving the rod, and
   a female threaded portion formed on an inner surface of the seat groove; and
   a locking bolt having:
   a male threaded portion formed on an outer periphery thereof which is threadedly engageable with the female threaded portion of the seat groove to engage and lock the rod to the head of the screw body, and
   a generally planar groove extending radially inwardly from the male threaded portion into a root of the locking bolt, the generally planar groove having a predetermined depth on the outer periphery of the locking bolt and a height less than a pitch of the male threaded portion.

7. The pedicle screw of claim 6, wherein the planar groove is formed to have a depth equal to about a half of a diameter of the locking bolt.

8. The pedicle screw of claim 6, wherein the predetermined depth is between ⅓ and ½ of a diameter of the locking bolt.

9. The pedicle screw of claim 6, wherein the female threaded portion has a generally inversed-trapezoidal cross section.

10. The pedicle screw as claimed in claim 6, wherein when the locking bolt is engaged with the head and the rod, a force resulting from the rod abutting the locking bolt is transferred to the male threaded portion to more closely engage the male threaded portion with the female threaded portion.

\* \* \* \* \*